United States Patent [19]
Edlich et al.

[11] Patent Number: 5,635,540
[45] Date of Patent: Jun. 3, 1997

[54] STABILIZED TOPICAL PHARMACEUTICAL PREPARATIONS

[75] Inventors: Richard F. Edlich; Sherry Sutton; George T. Rodeheaver, all of Charlottesville, Va.

[73] Assignee: The University of Virginia Patent Foundation, Charlottesville, Va.

[21] Appl. No.: 354,863

[22] Filed: Dec. 9, 1994

[51] Int. Cl.$^6$ .............................. A61K 47/34; A61K 9/10
[52] U.S. Cl. .................. 514/772.3; 514/817; 514/818; 514/816
[58] Field of Search ................ 514/772.3, 816, 514/817, 818

[56] References Cited

U.S. PATENT DOCUMENTS

| | | | |
|---|---|---|---|
| 4,529,601 | 7/1985 | Broberg et al. | 514/626 |
| 5,002,974 | 3/1991 | Geria | 514/782 |
| 5,298,260 | 3/1994 | Viegas et al. | 514/944 |
| 5,298,528 | 3/1994 | Evers | 514/626 |
| 5,346,903 | 9/1994 | Ackerman et al. | 514/282 |

*Primary Examiner*—Peter F. Kulkosky
*Attorney, Agent, or Firm*—Oblon, Spivak, McClelland, Maier & Neustadt, P.C.

[57] ABSTRACT

The present invention relates to stabilized topical pharmaceutical preparations. More specifically the present invention relates to a stabilized topical pharmaceutical preparation, based on the solubilization of a eutectic mixture of local anesthetic agents, in base form, which when combined in the presence of a surfactant and water produce a single phase hydrated polymer to be used in obtaining topical anesthesia and also relates to a stabilized antimicrobial topical pharmaceutical preparation.

10 Claims, No Drawings

STABILIZED TOPICAL PHARMACEUTICAL PREPARATIONS

BACKGROUND OF THE INVENTION

1. Field of the Invention

The present invention relates to stabilized topical pharmaceutical preparations. More specifically the present invention relates to a stabilized topical pharmaceutical preparation, based on the solubilization of a eutectic mixture of local anesthetic agents, in base form, which when combined in the presence of a surfactant and water produces a single phase hydrated polymer, to be used in obtaining topical anesthesia and also relates to a stabilized pharmaceutical preparation which is compatible with open wounds.

2. Discussion of the Background

Since their initial discovery, the formulation of topical pharmaceutical preparations have been investigated to address specific stability problems which arise with specific pharmaceutical agents.

Special stability problems have been noted in the area of local anesthetics and antimicrobial creams. In both instances, the availability of a stable preparation, with good bioavailability, has been lacking, despite the obvious need for such preparations. To date, the stability problems with each of these preparations has not been completely solved, necessitating preparation of such topical preparations shortly before use. This problem places a huge burden on hospital pharmacies, a burden which could be eased if a storage stable preparation could be developed.

Attempts have been made at obtaining stable topical anesthesia. One attempt involved the production of an anesthetically active film comprised of lidocaine in crystallized form. The problem with a solid carrier of this type is the inaccuracy in the dosage of anesthetic present in the carrier at any given time.

Further attempts have been made utilizing local anesthetically active compounds, in base form, while these compounds remain in crystalline form. The result has been that the desired anesthetic effect does not result. An attempt has also been made at a homogenous oil comprised of different anesthetic agents in base form. In such cases the active agents are not present in water soluble form. When placed in water, an oil in water emulsion results which is not stable or homogenous in composition.

Broberg et al (U.S. Pat. No. 4,529,601) report a pharmacologically active preparation of local anesthetics in the form of a eutectic mixture of two topical anesthetics, where one anesthetic has a melting point of 30° to 50° C. and the other has a melting point of above 30° C. The eutectic mixture is then administered in the form of an aqueous emulsion of an emulsifying agent and water. The disadvantage of this topical anesthetic is the general instability of emulsion preparations, which leads to inaccurate dosing when applied.

Specific problems in stability have also been noted in the area of topical antimicrobial and anti-fungal preparations. Such preparations are essential to the survival of severe burn victims.

In treating burn victims, it is typical to treat the open wounds with antimicrobial and anti-fungal agents such as a nitrofuran, polymyxin, nystatin or a mixture thereof. In the case of treating open wounds, such as burns, the carrier must also be non-damaging to the tissue. Polyoxyalkylene based carriers, such as a Poloxamer (Pluronic F-68 by BASF-Wyandott), are suitable based on their tissue non-toxicity.

However, pharmaceutical gels based on Poloxamer carriers are subject to low temperature phase separation, which decreases the usefulness of the preparation. Previous attempts have been made at obtaining stability in a Poloxamer gel, however, the results have been unsatisfactory. These attempts have involved increasing aeration during manufacturing, varying antimicrobial agents, and increasing temperature during manufacture. To date, unsatisfactory low temperature stability has been observed, as evidenced by the data in the table below, in which Poloxamer based preparations were prepared:

Time to phase transition of antimicrobial burn gel

| PRODUCT COMBINATION | TIME (minutes) 32-35° F. |
| --- | --- |
| Nystatin | 12 |
| Polymyxin | 10 |
| Nitrofurantoin | 13 |
| Nystatin/Polymyxin | 13 |
| Nystatin/Nitrofurantoin | 12 |
| Polymyxin/Nitrofurantoin | 10 |
| Nystatin/Polymyxin/Nitrofurantoin | 10 |

The problem with these gels is that a phase transition occurred at low temperatures resulting in inaccuracy of the dosage of antimicrobial agents due to their settling to the bottom of the container. Further attempts have been made utilizing bases other than Poloxamer and antimicrobial agents. Numerous problems with these preparations include the need to mechanically remove the preparation prior to a second application (silvadene), poor release of antimicrobial agents from the base (i.e poor bioavailability), damage to new tissue and lack of penetration in eschar (Vaseline based).

The purpose of this invention is to solubilize high concentrations of local anesthetic agents in base form to produce a stable hydrated polymer which can then be applied to the intended surface.

The purpose of this invention is also to provide a stabilized Poloxamer base to produce a stable gel to which antimicrobial agents and other pharmaceutical agents, can then be added.

SUMMARY OF THE INVENTION

Accordingly, one embodiment of the present invention is directed to a topical anesthetic preparation comprising:

A) 25 to 60 wt. % of a eutectic mixture of local anesthetic composition comprising:
  i) 40 to 75 wt. % of a first local anesthetic agent in base form having a melting point between 30° C. to 70° C.; and
  ii) 25 to 60 wt. % of a second local anesthetic in base form having a melting point above 30° C., wherein the sum of i) and ii) is 100%;

B) 20 to 50 wt. % of a surfactant; and

C) the balance water, wherein the composition is a single-phase.

According to a second embodiment of the invention prilocaine, in base form, is mixed with lidocaine in base form.

According to a third embodiment of the present invention an pharmaceutical cream is provided wherein a Poloxamer base, in the form of powder, is mixed with water, and caused to become hydrated, by subjecting the combination of Poloxamer base and water, to freezing temperatures, before a pharmaceutical agent is added. Antimicrobial agents with spectrums of gram positive organisms, gram negative organisms, anti-fungal agents or anesthetic agents can then be added.

According to a fourth embodiment of the invention the Poloxamer base comprises 80% polyoxyethylene units and 20% polyoxypropylene units.

DETAILED DESCRIPTION OF THE PREFERRED EMBODIMENTS

According to the topical anesthetic embodiment of the present invention, suitable local anesthetic agents having a melting point of 30° to 70° C. are prilocaine, tetracaine, butanilcaine and trimecaine.

Suitable local anesthetic agents having a melting point of above 30° C. are benzocaine, lidocaine, bupivocaine, dibucaine, mepivocaine and etidocaine, as well as tetracaine, butanilicaine and trimecaine.

The two local anesthetics which comprise the topical anesthetic are different, however a local anesthetic having a melting point above 30° C. may also be used as the agent having a melting point of from 30° to 70° C., provided that the local anesthetic has two local anesthetic agents, one with a melting point of 30° to 70° C. and a second with a melting point of above 30° C. Accordingly, tetracaine, butanilicaine or trimecaine are not used as both the local anesthetic agent having a melting point of 30° to 70° C. and the local anesthetic agent having a melting point of above 30° C.

Specifically preferred combinations of anesthetics are lidocaine/prilocaine and tetracaine/prilocaine. Eutectic mixture of local anesthetics are disclosed in Broberg et al. U.S. Pat. No. 4,529,601.

In accordance with the invention, a single phase topical anesthetic can be prepared by mixing:

i) a first local anesthetic agent in base form, with ii) a second local anesthetic in base form, wherein said first local anesthetic i) has a melting point of 30° C. to 70° C., preferably prilocaine and said second local anesthetic ii) has a melting point above 30° C., preferably lidocaine, in the presence of a surfactant, and water to produce a single phased mixture. When a surfactant and water are introduced into a mixture of the local anesthetic agents of i) and ii) in a water bath at a temperature of about 70° to 80° C., the agents solubilize to form a hydrated polymer.

The amount of anesthetic agents necessary to obtain a single phased mixture, will vary depending on the anesthetic agents used and the surfactant used. Generally the total amount of local anesthetic in the composition is from 25 to 60 wt. %, preferably from 30 to 50 wt. % of the total weight of the composition.

The amount of each anesthetic agent necessary to obtain a single phased mixture, will vary depending on the anesthetic agents used and the surfactant used. Generally the local anesthetic will comprise from 40 to 75 wt. %, preferably from 40 to 60 wt. %, of a local anesthetic melting between 30° to 70° C. and from 25 to 60 wt. %, preferably form 40 to 60 wt. % of a local anesthetic melting above 30° C., wherein the total amount of the two anesthetic is 100%.

The amount of surfactant necessary to obtain a single phased mixture, will vary depending on the anesthetic agents used and the surfactant used. Generally the total amount of surfactant in the composition is from 20 to 50 wt. %, preferably from 30 to 40 wt. % of the total weight of the composition.

The amount of water necessary to obtain a single phased mixture, will vary depending on the anesthetic agents used and the surfactant used. Preferably from 10 to 20 wt. % of water is used.

The local anesthetic composition of the present invention may further comprise suitable additives, such a pigment, a dye, an anti-oxidant, a stabilizer or a fragrance, provided that addition of such an additive does not destroy the single phase of the anesthetic composition.

Preferably, the hydrated local anesthetic mixture is prepared by melting the local anesthetic with the higher melting point of the two, followed by addition of the other local anesthetic, under vigorous mechanical mixing, such as trituration or grinding. A milky viscous liquid is formed, at which point, the surfactant is added with more mechanical mixing. Mixing of the surfactant produces a milky liquid of somewhat lower viscosity. Finally the balance of water is added under vigorous mechanical mixing. The material can then be transferred to an air tight container, after which a clear composition is obtained after about 60 minutes at room temperature.

Alternatively, the hydrated local anesthetic mixture can be prepared by first melting the lower melting local anesthetic, followed by addition of the other local anesthetic along with vigorous mechanical mixing, then addition of the surfactant and water as above. However, when the lower melting local anesthetic is melted first, the storage time needed to obtain the single phase composition, increases from about 1 hour to about 72 hours. Accordingly, the former method is preferred.

Suitable surfactants for preparing the hydrated topical anesthetic of the present invention are not particularly limiting. For example single-phase hydrated topical anesthetics can be prepared from anionic, cationic or non-ionic surfactants. Preferably non-ionic surfactants based on a polyol starter, which has been elaborated with alkylene oxide units such as ethylene oxide and propylene oxide such as ARLACEL™ and ARLATONE™ brand of non-ionic surfactants from Imperial Chemical Company and PLURONIC™ brand non-ionic surfactant from BASF-Wyandott. Specific examples include PLURONIC 188, ARLACEL 165 and ARLATONE 2121.

Evidence of the formation of a single-phase is supported by the following facts:

1. The mixture does not separate as would a microemulsion or oil/water mixture.
2. There are no birefringent bubbles suggesting any type of emulsion when using polarized light magnification up to 63Ox and differential interference contrast.
3. The clear gel, when coming in contact with water, will turn a whitish color. Under a 1:10 dilution, a cloudy solution will be produced which can be shown through the light scattering effect of a spectrophotometer to contain micelles of 679 nm diameter.

In accordance with the stabilized pharmaceutical preparation which is compatible with open wounds, a Poloxamer, preferably Pluronic F-68 is mixed with water at a ratio of from 1:0.8 to 1.2 w/w, preferably from 1:0.9 to 1.1, more preferably from 1:1. This combination is mixed in a large bowl until the powder has been wetted. The mixture is then placed in a freezer at 0° to 10° F., preferably 5° F., for at least 4 hours, preferably at least 6 hours, more preferably at least 8 hours, most preferably at least 12 hours. While in the freezer, the mixture will undergo phase transition to a liquid. The mixture is then removed from the freezer and warmed to room temperature. Pharmaceutical agents such as antimicrobial, antifungal and anesthetic agents are then added in the above mentioned concentrations.

The Poloxamer base used in preparing the topical antimicrobial preparation of the present invention is a polyoxyalkylene based polymer based on ethylene oxide and propylene oxide and comprises a series of closely related block polymers that may generally be classified as polyoxyethylene-polyoxypropylene condensates terminated in primary hydroxyl groups. They are formed by the condensation of propylene oxide onto a propylene glycol nucleus followed by condensation of ethylene oxide onto both ends of the polyoxypropylene base. The polyoxyethylene hydrophilic groups on the ends of the molecule are controlled in length to constitute anywhere from 10% to 90% by weight of the final molecule, preferably from 70–90 wt. % ethylene oxide, and 10–30 wt. % propylene oxide, even more preferably 80 wt. % ethylene oxide and 20 wt. % propylene oxide. The structure of the polyethylene-polypropylene nonionic surfactant is preferably HO—$(CH_2CH_2O)_x$—$(CH_2CHO)_4$—$(CH_2CH_2O)_x$—H.

The molecular weight Mn of the Poloxamer base is typically from 600 to 10,000, preferably from 1,000 to 9,000, more preferably from 5,000 to 8,500.

The present invention has been made, based on the discovery that Poloxamer base powder is not sufficiently hydrated upon simple combination with water, which causes a low temperature phase instability. Moreover, it has been discovered that a more complete hydration of the poloxamer power is not obtained by mere mechanical mixing measures, but rather a degree for hydration, sufficient to impart low temperature stability, is obtained by subjecting a combination of the Poloxamer base and water to reduced temperature, before the pharmaceutical agent is added.

After the Poloxamer base is hydrated, a pharmaceutical agent such as an anti-microbial, anti-fungal or anesthetic agent can be added. The pharmaceutical agent can be added to the stabilized Poloxamer base with stirring, and heating if necessary.

There is no particular limitation as to the specific antimicrobial or anti-fungal agent which can be added to the hydrated Poloxamer base. Suitable antimicrobial and antifungal agents are described in the *Merck Index, Fifth Edition* as antibacterials and antifungals, the entire contents of which are hereby incorporated by reference. In particular nitrofurans such as furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide and nitrofurazone (see also FURACIN), preferably nitrofurantoin and nitrofurazone can be used. However, nystatin, polymyxin and nitrofurantoin are especially preferred.

The anti-microbial preparation according to the present invention is not specifically limited in terms of the amount of pharmaceutical agent contained therein. The concentration of the pharmaceutical agent can be easily adjusted in order for application of the preparation to deliver a pharmaceutically effective amount. Generally a nitrofuran preparation will contain from 0.1 to 0.5 wt. % of a nitrofuran, preferably 0.2 to 0.3 wt. %. Especially preferable is a nitrofuran preparation containing from 0.2 to 0.3 wt. % of nitrofurantoin or nitrofurazone. A preparation of polymyxin B will contain from 0.1 to 1.0 wt. %. Preferably polymyxin B is added in an amount of 10,000 units/gm of Poloxamer. A preparation of nystatin will contain from 0.1 to 1.0 wt. %. Preferably nystatin is added in an amount of 4,000 units/gm of Poloxamer.

The antibiotic containing Poloxamer can be advantageously uses to treat burn victims, to prevent infection, or as a topical antiseptic agent.

In addition to or instead of the antibiotic mixture, the stabilized Poloxamer can comprise a local anesthetic such as benzocaine, lidocaine, bupivocaine, dibucaine, mepivocaine, etidocaine, tetracaine, butanilicaine and trimecaine. From 5 to 60 wt. % of a local anesthetic can be added. The antibiotic and anesthetic containing Poloxamer can be advantageously used to treat burn victims, to prevent infection and provide temporary pain relief. The anesthetic containing Poloxamer, both with or without the antibiotic, can also be advantageously used as a surgical anesthetic, on open wounds, during surgery.

Having generally described this invention, a further understanding can be obtained by reference to certain specific examples which are provided herein for purposes of illustration only and are not intended to be limiting unless otherwise specified.

The present invention will be described more in detail with reference to a number of examples.

EXAMPLES A–G

Anesthetic compositions were prepared as follows:

A motor was placed in a water bath heated to 70°–74° C. and allowed to equilibrate. The local anesthetic with the higher melting point was added and melted, followed by addition of the second anesthetic. The mixture was triturated until a milky viscous liquid was formed. The indicated amount of surfactant was then added, triturated further until a less viscous yet milky liquid is formed. Finally water was added by syringe, and triturated further. The mixture is then transferred to an air tight storage container and allowed to stand for about 60 minutes.

TABLE 1

| anesthetic | 20 wt. % solution of polymer in anesthetic | | | | | | |
|---|---|---|---|---|---|---|---|
| | A | B | C | D | E | F | G |
| 40% lidocaine/60% prilocaine | S | $S_s$ | $S_s$ | S | S | $S_2$ | $S_2$ |
| 50% lidocaine/50% prilocaine | N | | | | | | |
| 60% lidocaine/40% prilocaine | S | | | | | | |
| 25% lidocaine/75% prilocaine | S | | | | | | |
| 30% lidocaine/70% prilocaine | S | | | | | | |
| 40% lidocaine/60% prilocaine* | S | | | | | | |
| 40% lidocaine/60% tetracaine | N | | | | | | |
| 60% prilocaine/40% tetracaine | S | | | | | | |
| mepivocaine HCl | N | | | N | | $S_2$ | |
| prilocaine HCl | N | | | N | | N | |
| lidocaine HCl | S | | | N | | $S_2$ | |
| lidocaine free base | | | | N | | N | |
| prilocaine free base | | | | N | | N | |

A: pluronic
B: arlatone 269
C: Arlatone 2121
D: ethylhexabenzyl ammonium bromide
E: benzyl chloride
F: Na DSS
G: Sodium lauryl sulfonate
S: homogeneously soluble
N: insoluble
$S_2$: soluble, biphasic
$S_s$: soluble, solidifying when cooled The test of analgesia was executed using gradually increasing electric impulses delivered to the tongues of the subjects being tested. As the impulses were delivered the subjects were asked to indicate when they began to have sensation. The present invention was then applied to the subject's tongue. The subject was then asked to indicate when he experienced pain comparable to that caused by the previous delivery of impulses without anesthesia. The time required to prevent the subject from feeling the full range of impulses was recorded as the initiation time of anesthesia. All of the cases were anesthetized in 45 seconds or less. Tests were taken periodically until the anesthetic no longer allowed for the full range of impulses. In all cases the anesthetic effect remained for over 45 minutes.

EXAMPLE 2

Prilocaine,base 1.4 g (31.5% of solution)
Benzocaine,base 0.6 g (13.5% of solution)
surfactant 1.33 g (30% of solution))
water 1.1 g (25% of solution)

The above combination of anesthetically active agents failed to form a clear solution containing a hydrated polymer. The addition of water and surfactant to the agents while in a 70° C. water bath resulted in a white paste.

EXAMPLE 3

5,000 g of Pluronic F-68 and 4,900 mL of filtered sterilized and deionized water were mixed for about 5 minutes, until the Pluronic powder was thoroughly wetter, then stored at 5° F. for 16 h. In a separate container, an anti-microbial mixture was prepared of 32 g of nitrofurantoin powder (Bolar Pharmaceutical), 473 mL of Nystatin suspension (100,000 units/mL), 250 mL of Polymyxin solution (13.62 gms of polymyxin from Pfizer Inc.) and 100 mL of filtered, sterilized and deionized water by mixing under mechanical mixing. A homogenous mixture of the antibiotics were slowly poured into the aqueous Pluronic F-68, rinsing with 100 mL of water (filtered, sterilized and deionized). The Pluronic and antibiotic solutions were stirred slowly and continuously at from 17° to 19° C., wherein a cream was formed after about 2 to 2.5 h. The resulting cream was stored at from 25° to 30° C. until use.

2) Stability of base after subjecting to low temperature stabilization

| °F. | 1 Day | 1 Week | 1 Month | 4 Months |
|---|---|---|---|---|
| 35° | S | S | S | S |
| 45° | S | S | S | S |
| 60° | S | S | S | S |
| 78° | S | S | S | S |
| 91° | S | S | S | S |

S = Stable
U = Unstable

The data shows that by subjecting the Pluronic to freezing temperatures, the resulting cream is freely stable over a wide temperature range.

EXAMPLE 4

Pluronic F-68 and sterile, filtered and deionized water were mixed 1:1 w/w and stirred at ambient temperature until thoroughly wetted. One sample was desiccated immediately, while the other was subjected to freezing for 14–16 h before desiccation.

3) Weight of comparison bases before and after desiccation base weight of sample immediately desiccated after preparation vs. sample stored in freezer before desiccation

|  | Sample immediately desiccated | Sample stored in freezer |
|---|---|---|
| 3/24/94 (initial wt) | 50 grams | 50 grams |
| 4/4/94 | 27.66 grams | 30.44 grams |
| 4/8/94 | 24.89 grams | 27.34 grams |

The data shows that by subjecting the Pluronic F-68 to freezing conditions, there is an additional water which can not be removed by simple desiccation.

COMPARATIVE EXAMPLE 1

The same preparation of Example 3 was prepared, except the Pluronic F-68 was used directly, after the having been thoroughly wetted with water. No freezing treatment was used.

| °F. | 1 Day | 1 Week | 1 Month | 4 Months |
|---|---|---|---|---|
| 35° | U | U | U | U |
| 45° | S | S | S | U |
| 60° | S | S | S | U |
| 78° | S | S | S | U |
| 91° | S | S | S | U |

S = Stable
U = Unstable

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A phase stabilized pharmaceutical carrier consisting essentially of a major amount of:
   i) a Poloxamer base of a polyoxyethylene-polyoxypropylene condensate of Mn 600–10,000; and
   ii) water,
   wherein said pharmaceutical carrier is phase stabilized by subjecting said Poloxamer base and water at a ratio of Poloxamer base to water of from 1:0.8 to 1.2 w/w, to a temperature of from 0° to 10° F.

2. The stabilized pharmaceutical carrier of claim 1, wherein said Poloxamer base comprises 70 to 90 wt. % ethylene oxide units and 10 to 30 wt. % propylene oxide units.

3. The stabilized pharmaceutical carrier of claim 1, wherein said composition contains 0.8 to 1.2 parts water per part of Poloxamer.

4. A phase stabilized pharmaceutical preparation comprising:
   A) a carrier consisting essentially of a major amount of
      i) a Poloxamer base of a polyoxyethylene-polyoxypropylene condensate of Mn 600–10,000;
      ii) water; and
   B) a pharmaceutical agent selected from the group consisting of an antibiotic, an anti-fungal and a mixture thereof
   wherein said pharmaceutical preparation is phase stabilized by subjecting said Poloxamer base and water at a ratio of Poloxamer base to water of from 1:0.8 to 1.2 w/w, to a temperature of from 0° to 10° F., prior to addition of said pharmaceutical agent.

5. The stabilized pharmaceutical preparation of claim 4, wherein said Poloxamer base comprises 70 to 90 wt. % ethylene oxide units and 10 to 30 wt. % propylene oxide units.

6. The stabilized pharmaceutical preparation of claim 4, wherein said composition contains 0.8 to 1.2 parts water per part of Poloxamer.

7. The stabilized pharmaceutical preparation of claim 4, wherein said pharmaceutical agent is selected from the group consisting of nitrofurantoin, nystatin, polymyxin and a mixture thereof.

8. The stabilized pharmaceutical preparation of claim 4, wherein said pharmaceutical agent further comprises an anesthetic.

9. The stabilized pharmaceutical preparation of claim 8, wherein said anesthetic is selected from the group consisting of benzocaine, lidocaine, bupivocaine, dibucaine, mepivocaine, etidocaine, tetracaine, butanilicaine, trimecaine and a mixture thereof.

10. The stabilized pharmaceutical preparation of claim 4, wherein said pharmaceutical agent is selected from the group consisting of furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide and nitrofurazone.

* * * * *